US011867896B2

(12) United States Patent
Usuda

(10) Patent No.: US 11,867,896 B2
(45) Date of Patent: Jan. 9, 2024

(54) ENDOSCOPE SYSTEM AND MEDICAL IMAGE PROCESSING SYSTEM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 500 days.

(21) Appl. No.: 17/169,533

(22) Filed: Feb. 7, 2021

(65) Prior Publication Data
US 2021/0161366 A1 Jun. 3, 2021

Related U.S. Application Data

(63) Continuation of application No. PCT/JP2019/031134, filed on Aug. 7, 2019.

(30) Foreign Application Priority Data

Aug. 20, 2018 (JP) ................................. 2018-154055

(51) Int. Cl.
*G02B 23/24* (2006.01)
*A61B 1/00* (2006.01)

(52) U.S. Cl.
CPC ...... *G02B 23/2446* (2013.01); *A61B 1/00006* (2013.01); *A61B 1/00045* (2013.01); *A61B 1/000094* (2022.02)

(58) Field of Classification Search
None
See application file for complete search history.

(56) References Cited

U.S. PATENT DOCUMENTS

| 2007/0066866 | A1* | 3/2007 | Noguchi | A61B 1/00128 600/101 |
| 2011/0254937 | A1 | 10/2011 | Yoshino | |
| 2011/0301443 | A1 | 12/2011 | Yamaguchi et al. | |
| 2011/0319711 | A1 | 12/2011 | Yamaguchi et al. | |
| 2017/0224221 | A1* | 8/2017 | Matsumoto | A61B 1/00167 |
| 2018/0325356 | A1* | 11/2018 | Tateshita | A61B 1/00045 |

(Continued)

FOREIGN PATENT DOCUMENTS

| CN | 102247116 | 11/2011 |
| EP | 3991632 A1 * | 5/2022 |

(Continued)

OTHER PUBLICATIONS

Office Action of Japan Counterpart Application, with English translation thereof, dated Aug. 9, 2022, pp. 1-8.

(Continued)

*Primary Examiner* — Michael Lee
(74) *Attorney, Agent, or Firm* — JCIPRNET

(57) ABSTRACT

A region of interest located in a first part to be observed is detected from a medical image at a first timing. In a case where a tip portion of an endoscope moves from the first part to be observed toward a second part to be observed and then moves to the first part to be observed again, a return determination unit performs first determination processing for determining whether the tip portion has returned to the first part to be observed, by using a medical image acquired a second timing. A display control unit performs display control of a monitor by using a determination result of the return determination unit.

14 Claims, 9 Drawing Sheets

(56) References Cited

U.S. PATENT DOCUMENTS

| | | | |
|---|---|---|---|
| 2019/0114738 A1 | 4/2019 | Sonoda | |
| 2019/0239718 A1* | 8/2019 | Iwaki | G02B 23/2461 |
| 2020/0058124 A1* | 2/2020 | Iwaki | A61B 1/00045 |
| 2020/0065970 A1* | 2/2020 | Sonoda | A61B 1/000094 |
| 2020/0237184 A1* | 7/2020 | Shigeta | A61B 1/0005 |
| 2021/0153720 A1* | 5/2021 | Usuda | A61B 1/07 |

FOREIGN PATENT DOCUMENTS

| | | | |
|---|---|---|---|
| JP | 2004358094 A * | 12/2004 | |
| JP | 2011224038 | 11/2011 | |
| JP | 2011254936 | 12/2011 | |
| JP | 2011255006 | 12/2011 | |
| JP | 2012010733 | 1/2012 | |
| JP | 2012170641 | 9/2012 | |
| JP | 2012170774 | 9/2012 | |
| WO | WO-2014136576 A1 * | 9/2014 | A61B 1/00009 |
| WO | 2017073337 | 5/2017 | |
| WO | 2017216922 | 12/2017 | |
| WO | WO-2018159363 A1 * | 9/2018 | A61B 1/00009 |
| WO | 2019106712 | 6/2019 | |

OTHER PUBLICATIONS

"Search Report of Europe Counterpart Application", dated Sep. 15, 2021, p. 1-p. 9.

"International Search Report (Form PCT/ISA/210) of PCT/JP2019/031134," dated Nov. 5, 2019, with English translation thereof, pp. 1-5.

"Written Opinion of the International Searching Authority (Form PCT/ISA/237) of PCT/JP2019/031134," dated Nov. 5, 2019, with English translation thereof, pp. 1-12.

Office Action of China Counterpart Application, with English translation thereof, dated Sep. 7, 2023, pp. 1-14.

* cited by examiner

ENDOSCOPE SYSTEM AND MEDICAL IMAGE PROCESSING SYSTEM

CROSS-REFERENCE TO RELATED APPLICATIONS

This application is a Continuation of PCT International Application No. PCT/JP2019/031134 filed on 7 Aug. 2019, which claims priority under 35 U.S.C. § 119(a) to Japanese Patent Application No. 2018-154055 filed on 20 Aug. 2018. The above application is hereby expressly incorporated by reference, in its entirety, into the present application.

BACKGROUND OF THE INVENTION

1. Field of the Invention

The present invention relates to an endoscope system and a medical image processing system using an analysis result of a medical image.

2. Description of the Related Art

In the current medical field, medical image processing systems using medical images, such as an endoscope system including a light source device, an endoscope, and a processor device, are widely used. In recent years, diagnostic information regarding the state of a disease has been acquired by extracting a region of interest containing a potential lesion portion from a medical image and performing image analysis on the extracted region of interest.

For example, in WO2017/216922A (corresponding to US2019/0114738A1), an image of a region of interest detected from a medical image is stored, and the stored image of the region of interest is displayed in a part different from a part to be observed displaying the medical image at a timing at which the detection of the region of interest on the medical image is interrupted/ceased. In JP2012-10733A (corresponding to US2011/0319711A1), blood vessel information obtained when a region of interest is detected is stored. Accordingly, even if the region of interest has disappeared from a screen, it is possible to return to the position of the region of interest again by using the stored blood vessel information as a clue. In WO2017/073337A, when a region of interest is detected, a still image of the region of interest is displayed in a region different from a region displaying an observation image used for observation by a user.

SUMMARY OF THE INVENTION

In an endoscopic examination using an endoscope system, in order to detect a region of interest such as a lesion, as in screening, a tip portion of an endoscope is inserted to the deepest position, and then the tip portion is gradually moved and removed. If the tip portion momentarily passes through a part to be observed where the region of interest is present during the removal, the user may not notice the region of interest even though the region of interest is automatically detected. Even if the user notices the region of interest, it may be difficult for the tip portion to return to the part to be observed where the region of interest is present due to a change in the shape of the observation target around the region of interest. It has therefore been required to support a user in returning a tip portion of an endoscope to a part to be observed where a region of interest overlooked by the user is present. JP2012-10733A describes that the tip portion returns to the position of the region of interest again when passing through the region of interest. However, as described above, because of a change in the shape of the observation target around the region of interest, it may be difficult for the tip portion to return to the position of the region of interest without any support in returning the tip portion to the position of the region of interest.

It is an object of the present invention to provide an endoscope system and a medical image processing system capable of supporting a user in returning a tip portion of an endoscope to a part to be observed where a region of interest overlooked by the user is present.

An endoscope system of the present invention includes an endoscope, a medical image acquisition unit, a region-of-interest detection unit, a first determination unit, and a display control unit. The endoscope has disposed in a tip portion thereof an imaging element that performs imaging of an observation target and outputs a medical image. The medical image acquisition unit acquires the medical image. The region-of-interest detection unit detects a region of interest located in a first part to be observed within the observation target from a medical image acquired at a first timing. In a case where the tip portion moves away from the first part to be observed and moves toward a second part to be observed different from the first part to be observed, and then the tip portion moves away from the second part to be observed and moves toward the first part to be observed, the first determination unit performs first determination processing for determining whether the tip portion has returned to the first part to be observed, by using a medical image acquired at a second timing different from the first timing. The display control unit performs display control of a display unit by using a determination result of the first determination unit.

Preferably, the first determination unit performs the first determination processing by using a similarity between the medical image at the first timing and the medical image at the second timing. Preferably, the first determination unit determines that the tip portion has returned to the first part to be observed when the similarity is greater than or equal to a first-determination similarity. Preferably, the first determination unit determines that the tip portion has returned to the first part to be observed when the similarity is greater than or equal to a first-determination similarity and the region-of-interest detection unit detects the region of interest in the first part to be observed.

Preferably, the endoscope system further includes a second determination unit that performs second determination processing for determining whether the region of interest in the first part to be observed is overlooked, and the display control unit performs the display control by using the determination result of the first determination unit and a determination result of the second determination unit. Preferably, the second determination unit performs the second determination processing by using at least one of a first time period or a second time period, the first time period indicating a time period from when the region of interest in the first part to be observed is detected to when the region of interest disappears from the display unit, the second time period indicating a time period that begins after the region of interest disappears from the display unit.

Preferably, the second determination unit determines that the region of interest in the first part to be observed is overlooked when the first time period is shorter than a second-determination first time period. Preferably, the second determination unit determines that the region of interest in the first part to be observed is overlooked when the first time period is shorter than a second-determination first time period and the second time period is longer than or equal to a second-determination second time period. Preferably, the second determination unit determines that the region of interest in the first part to be observed is overlooked when a similarity between the medical image acquired by the medical image acquisition unit and the medical image at the first timing is lower than a second-determination similarity. Preferably, the second determination unit performs the second determination processing by using at least one of a first time period or a second time period and a similarity between the medical image acquired by the medical image acquisition unit and the medical image at the first timing, the first time period indicating a time period from when the region of interest in the first part to be observed is detected to when the region of interest disappears from the display unit, the second time period indicating a time period that begins after the region of interest disappears from the display unit.

Preferably, the display control unit performs display control for a region-of-interest image at an oversight determination timing at which it is determined in the second determination processing that the region of interest in the first part to be observed is overlooked and at a return determination timing at which it is determined that the tip portion has returned to the first part to be observed, the region-of-interest image being an image displaying the region of interest in the first part to be observed. Preferably, the display control unit starts displaying the region-of-interest image at the oversight determination timing and keeps displaying the region-of-interest image during a period from the oversight determination timing to the return determination timing. Preferably, the display control unit hides the region-of-interest image at the return determination timing. Preferably, the display control unit displays an enhanced image at the return determination timing, the enhanced image being obtained by performing enhancement processing on the region-of-interest image.

A medical image processing system of the present invention includes a medical image acquisition unit, a region-of-interest detection unit, a first determination unit, and a display control unit. The medical image acquisition unit acquires a medical image obtained by imaging of an observation target, and the region-of-interest detection unit detects a region of interest located in a first part to be observed within the observation target from a medical image acquired at a first timing. The first determination unit performs first determination processing for determining whether a medical image acquired at a second timing different from the first timing includes at least a portion of an image of the first part to be observed. The display control unit performs display control of a display unit by using a determination result of the first determination unit.

According to the present invention, it is possible to support a user in returning a tip portion of an endoscope to a part to be observed where a region of interest overlooked by the user is present.

BRIEF DESCRIPTION OF THE DRAWINGS

FIG. 1 is a block diagram illustrating an image processing system, an endoscope system, and so on;

DESCRIPTION OF THE PREFERRED EMBODIMENTS

Figure 1:
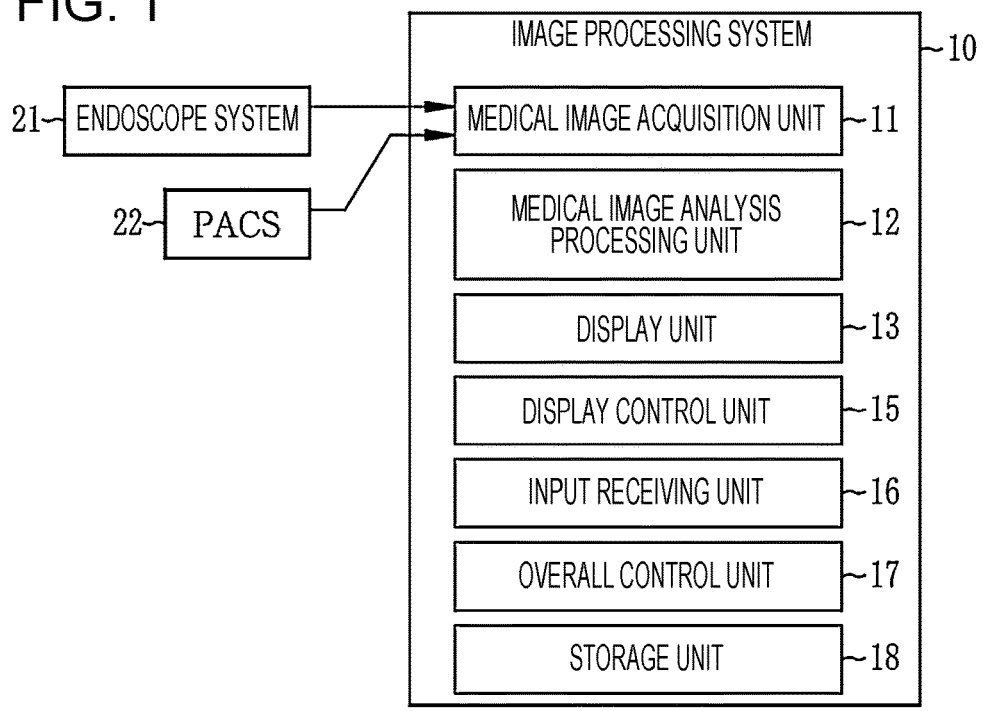

As illustrated in FIG. 1, an image processing system 10 includes a medical image acquisition unit 11, a medical image analysis processing unit 12, a display unit 13, a display control unit 15, an input receiving unit 16, an overall control unit 17, and a storage unit 18.

The medical image acquisition unit 11 acquires a medical image including a photographic subject image directly from an endoscope system 21 or the like that is a medical apparatus, or via a management system such as a PACS (Picture Archiving and Communication System) 22 or any other information system. The medical image is a still image or a moving image (so-called examination moving image). When the medical image is a moving image, the medical image acquisition unit 11 can acquire, as still images, frame images constituting the moving image after an examination. When the medical image is a moving image, furthermore, displaying the medical image includes displaying a still image of one representative frame constituting the moving image, and reproducing the moving image one or a plurality of times. The medical image acquired by the medical image acquisition unit 11 includes an image captured by a doctor using a medical apparatus such as the endoscope system 21, and an image automatically captured by the medical apparatus such as the endoscope system 21 regardless of an image-capturing instruction given by the doctor. In this embodiment, since the image processing system 10 and the endoscope system 21 perform image processing using a medical image, both the image processing system 10 and the endoscope system 21 correspond to a medical image processing system. The medical image system also includes an ultrasound diagnostic apparatus that acquires and displays an image in real time.

When a plurality of medical images can be acquired, the medical image acquisition unit 11 can selectively acquire one or a plurality of medical images among these medical images. Further, the medical image acquisition unit 11 can acquire a plurality of medical images acquired in a plurality of different examinations. For example, the medical image acquisition unit 11 can acquire either or both of a medical image acquired in an examination performed in the past and a medical image acquired in the latest examination. That is, the medical image acquisition unit 11 can arbitrarily acquire a medical image.

In this embodiment, a plurality of medical images including photographic subject images are acquired. More specifically, in a case where a medical image captured in a single specific examination is acquired and there is a plurality of medical images captured in a single specific examination, a plurality of medical images are acquired from among the series of medical images. In this embodiment, furthermore, the image processing system 10 is connected to the endoscope system 21 to acquire a medical image from the endoscope system 21. That is, in this embodiment, a medical image is an endoscopic image.

The display unit 13 is a display that displays the medical image acquired by the medical image acquisition unit 11 and an analysis result obtained by the medical image analysis processing unit 12. A monitor or display included in a device to which the image processing system 10 is connected can be shared and used as the display unit 13 of the image processing system 10. The display control unit 15 controls a display style of the medical image and the analysis result on the display unit 13.

The input receiving unit 16 accepts an input from a mouse, a keyboard, or any other operating device connected to the image processing system 10. The operation of the units of the image processing system 10 can be controlled using these operating devices.

The overall control unit 17 performs overall control of the operation of the units of the image processing system 10. When the input receiving unit 16 receives an operation input using an operating device, the overall control unit 17 controls the units of the image processing system 10 in accordance with the operation input.

The storage unit 18 stores a still image or the like of a medical image in a storage device (not illustrated) such as a memory included in the image processing system 10 or in a storage device (not illustrated) included in the medical apparatus such as the endoscope system 21 or the PACS 22.

Figure 2:
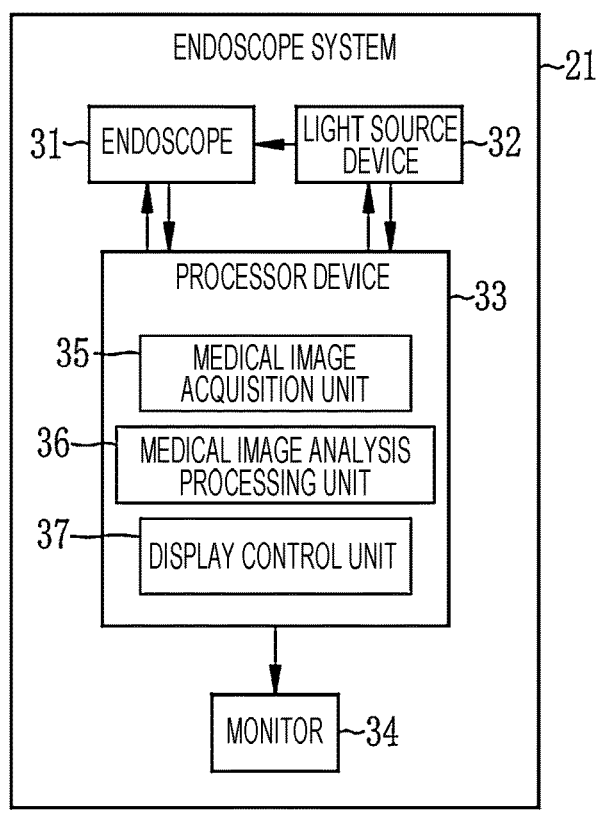
FIG. 2 is a block diagram illustrating the endoscope system.

As illustrated in FIG. 2, in this embodiment, the endoscope system 21 to which the image processing system 10 is connected includes an endoscope 31 that captures an image of a photographic subject irradiated with at least one of light in the white wavelength range or light in a specific wavelength range to acquire an image, a light source device 32 that irradiates the inside of the photographic subject with illumination light via the endoscope 31, a processor device 33, and a monitor 34 that displays a medical image such as an endoscopic image captured using the endoscope 31. The light in the specific wavelength range to be used as illumination light by the endoscope 31 is, for example, light in a shorter wavelength range than the green wavelength range and is, in particular, light in the blue range or violet range in the visible range.

The processor device 33 includes a medical image acquisition unit 35, a medical image analysis processing unit 36, and a display control unit 37. The medical image acquisition unit 35 acquires the medical image output from the endoscope 31. The medical image analysis processing unit 36 performs analysis processing on the medical image acquired by the medical image acquisition unit 35. The content of the processing performed by the medical image analysis processing unit 36 is similar to the content of the processing performed by the medical image analysis processing unit 12 of the image processing system 10. The display control unit 37 displays the medical image obtained by the medical image analysis processing unit 36 on the monitor 34 (display unit). The processor device 33 is connected to the image processing system 10. The medical image acquisition unit 35 is similar to the medical image acquisition unit 11, the medical image analysis processing unit 36 is similar to the medical image analysis processing unit 12, and the display control unit 37 is similar to the display control unit 15.

Figure 3:
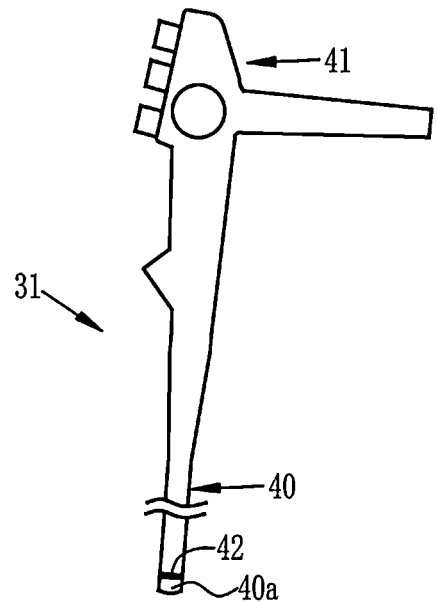
FIG. 3 is a schematic diagram illustrating an endoscope.

As illustrated in FIG. 3, the endoscope 31 includes an insertion section 40 to be inserted into a subject, and an operation section 41 disposed in a proximal end portion of the insertion section 40. The insertion section 40 has disposed in a tip portion 40a thereof an imaging element 42 that performs imaging of an observation target in the subject. A medical image obtained by the imaging element 42 through imaging is transmitted to the processor device 33.

Figure 4:
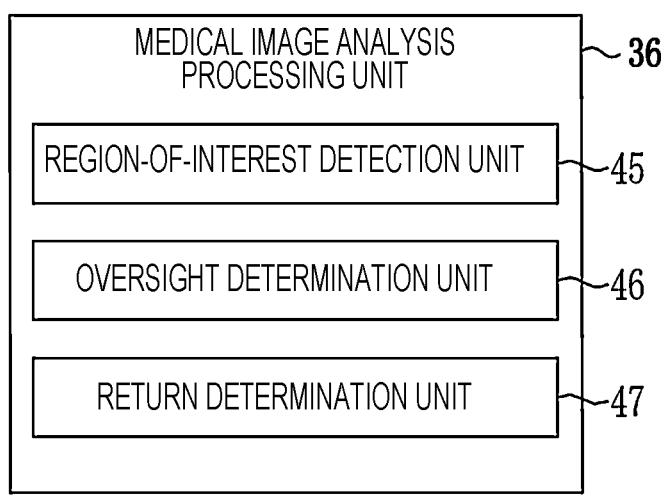
FIG. 4 is a block diagram illustrating the functions of a medical image analysis processing unit.

The medical image analysis processing unit 36 performs analysis processing using the medical image acquired by the medical image acquisition unit 35. As illustrated in FIG. 4, the medical image analysis processing unit 36 includes a region-of-interest detection unit 45, an oversight determination unit 46 (second determination unit), and a return determination unit 47 (first determination unit). The region-of-interest detection unit 45 performs region-of-interest detection processing for detecting a region of interest from the medical image. When a region of interest is detected, a region-of-interest image displaying the region of interest is stored in an image storage unit (not illustrated) in the processor device 33. Examples of the region-of-interest detection processing include NN (Neural Network), CNN (Convolutional Neural Network), AdaBoost, and random forest. Alternatively, the region-of-interest detection processing may involve detecting a region of interest on the basis of a feature value obtained as color information of the medical image, the gradient of pixel values, or the like. The gradient of pixel values or the like changes according to, for example, the shape of the photographic subject (such as generalized ups and downs or localized depression or elevation in a mucous membrane), color (color such as from inflammation, bleeding, redness, or whitening caused by atrophy), tissue characteristics (such as the thickness, depth, or density of blood vessels, or a combination thereof), structural characteristics (such as pit pattern), or the like.

The region of interest detected by the region-of-interest detection unit 45 is a region including, for example, a lesion portion such as a cancer, a benign tumor portion, an inflammation portion (including, in addition to so-called inflammations, a portion with a change such as bleeding or atrophy), a colon diverticulum, a treatment mark (an EMR (Endoscopic mucosal resection) scar, an ESD (Endoscopic Submucosal Dissection) scar, or a clip location), a bleeding point, a perforated hole, a vascular anomaly, an ablation mark by heating, a marking portion marked by coloring with a coloring agent, a fluorescent agent, or the like, or a biopsy-performing portion subjected to a biopsy. That is, a region including a lesion, a region of a potential lesion, a region subjected to some treatment such as a biopsy, a treatment tool such as a clip or forceps, a region requiring detailed observation regardless of the possibility of a lesion, such as a dark region (a region where observation light is difficult to reach because of the back of the fold or the back of the lumen), or the like can be a region of interest. In the endoscope system 21, the region-of-interest detection unit 45 detects, as a region of interest, a region including at least one of a lesion portion, a benign tumor portion, an inflammation portion, a colon diverticulum, a treatment mark, a bleeding point, a perforated hole, a vascular anomaly marking portion, or a biopsy-performing portion.

Figure 5:
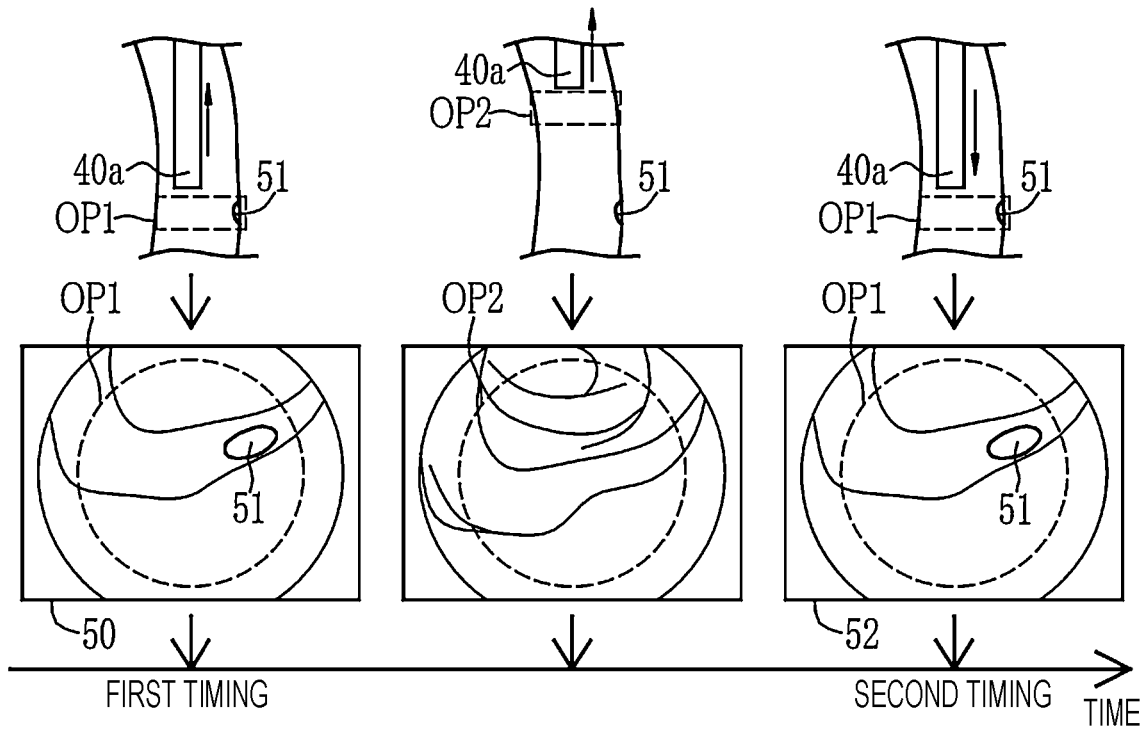
FIG. 5 is an explanatory diagram illustrating that a tip portion of the endoscope moves from a first part to be observed to a second part to be observed and then returns to the first part to be observed.

As illustrated in FIG. 5, in a medical image 50 acquired at a first timing, when a region of interest 51 in a first part to be observed OP within the observation target is detected by the region-of-interest detection unit 45, the oversight determination unit 46 performs oversight determination processing (second determination processing) for determining whether the user has overlooked the region of interest 51. The details of the oversight determination processing will be described below. The return determination unit 47 performs return determination for determining whether the tip portion 40*a* has returned to the original, first part to be observed OP1 in response to the user noticing an oversight of the region of interest and moving the tip portion 40*a* of the endoscope 31.

When the region-of-interest detection unit 45 detects the region of interest 51 but the user does not notice the presence of the region of interest 51, the tip portion 40*a* of the endoscope 31 moves away from the first part to be observed OP1 and moves toward a second part to be observed OP2 different from the first part to be observed OP1 After that, when the user notices that the region of interest 51 has been overlooked, the tip portion 40*a* moves away from the second part to be observed OP2 and moves toward the first part to be observed OP1 in accordance with the user's operation. Then, the return determination unit 47 determines whether the tip portion 40*a* has returned to the original, first part to be observed OP1 by using a medical image 52 acquired at a second timing at which the tip portion 40*a* moves toward the first part to be observed OP1. That is, the return determination unit 47 performs return determination processing (first determination processing) for determining whether the medical image 52 at the second timing includes at least a portion of an image of the first part to be observed OP1. The return determination processing is continuously performed at certain intervals from an oversight determination timing. The details of the return determination processing will be described below.

As described above, examples of the situation where the region of interest is overlooked include lesion screening, which is performed while the tip portion 40*a* of the endoscope 31 is moved within the subject. In lesion screening, depending on the speed of the movement of the tip portion 40*a* of the endoscope 31, the tip portion 40*a* may pass through the position of region of interest without the user noticing the region of interest. In this case, the region of interest is overlooked.

The reason that the return determination is performed is that since the shape of the digestive tract into which the endoscope 31 is inserted is easily changed by an operation such as air supply, the region of interest such as a lesion may be hidden by the shape of the digestive tract. For this reason, not only visual observation by the user but also automatic determination by the return determination unit 47 is used to ensure that the tip portion 40*a* can return to the original, first part to be observed OP1.

Figure 6:
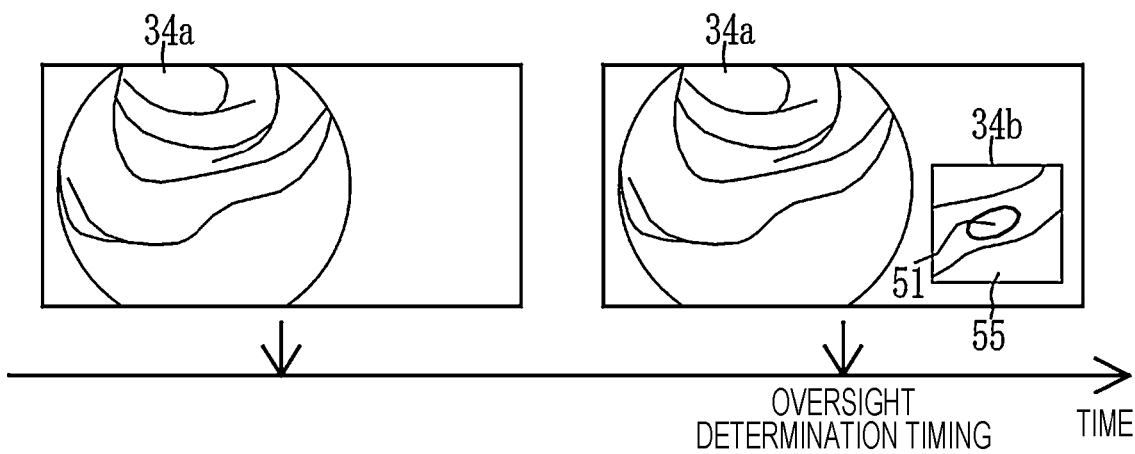
FIG. 6 is an explanatory diagram illustrating that a region-of-interest image is displayed at an oversight determination timing.

When the oversight determination unit 46 performs oversight determination processing, the display control unit 37 performs display control of the monitor 34 by using a determination result of the oversight determination unit 46. At an oversight determination timing at which the oversight determination unit 46 determines that the region of interest in the first part to be observed OP1 is overlooked, as illustrated in FIG. 6, the display control unit 37 starts displaying a region-of-interest image 55, which displays the region of interest 51 in the first part to be observed OP1, in a second display region 34*b* different from a first display region 34*a* of the monitor 34 where the medical image is displayed. This allows the user to return the tip portion 40*a* of the endoscope 31 to the first part to be observed OP1 where the region of interest 51 is overlooked by operating the endoscope 31 while comparing the medical image in the first display region 34*a* and the region-of-interest image 55 in the second display region 34*b*.

If the oversight determination unit 46 determines that the region of interest in the first part to be observed OP1 is not overlooked, the region-of-interest image 55 is not displayed in the second display region 34*b*. It is preferable to keep displaying the region-of-interest image 55 in the second display region 34*b* at least during a period from the oversight determination timing to a return determination timing described below.

Figure 7:
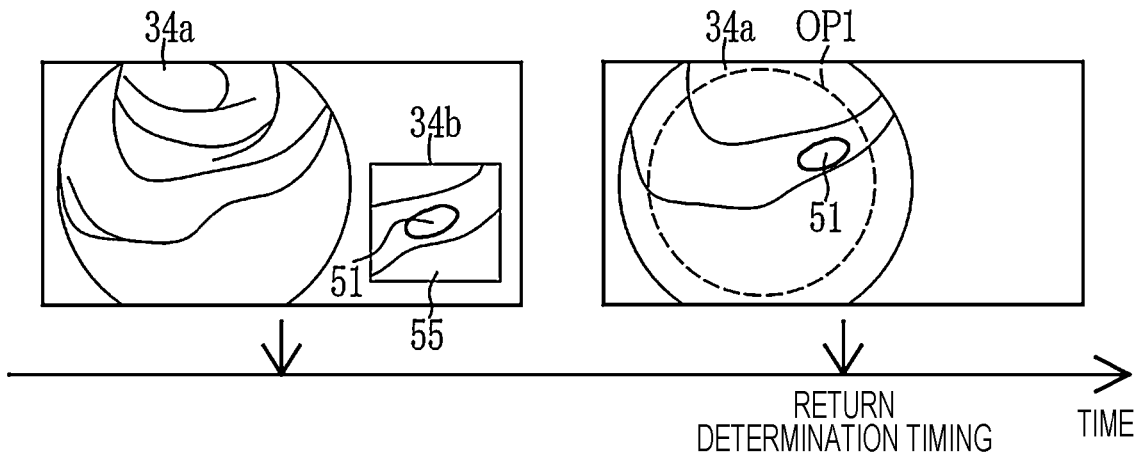
FIG. 7 is an explanatory diagram illustrating that the region-of-interest image is hidden at a return determination timing.
Figure 8:
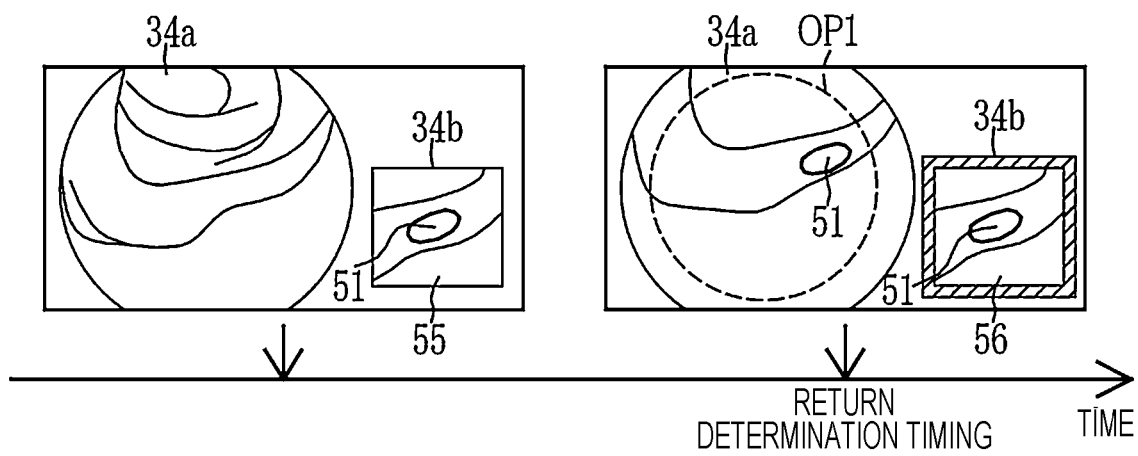
FIG. 8 is an explanatory diagram illustrating that an enhanced image is displayed at the return determination timing.

When the return determination unit 47 performs return determination processing, the display control unit 37 performs display control of the monitor 34 by using the determination result of the return determination unit 47. At a return determination timing at which the return determination unit 47 determines that the tip portion 40*a* of the endoscope 31 has returned to the first part to be observed OP1, as illustrated in FIG. 7, it is preferable that the display control unit 37 hide the region-of-interest image 55 that is kept displayed after the oversight determination timing. This allows the user to grasp that the tip portion 40*a* has returned to the original, first part to be observed OP1. In addition, after the observation of the region of interest in the first part to be observed OP is resumed, unnecessary information is removed from the monitor 34, which prevents a reduction in the user's desire to observe. At the return determination timing, as illustrated in FIG. 8, the display control unit 37 may display, in the second display region 34*b*, an enhanced image 56 obtained by performing enhancement processing on the outer edge or the like of the region-of-interest image 55.

Figure 9:
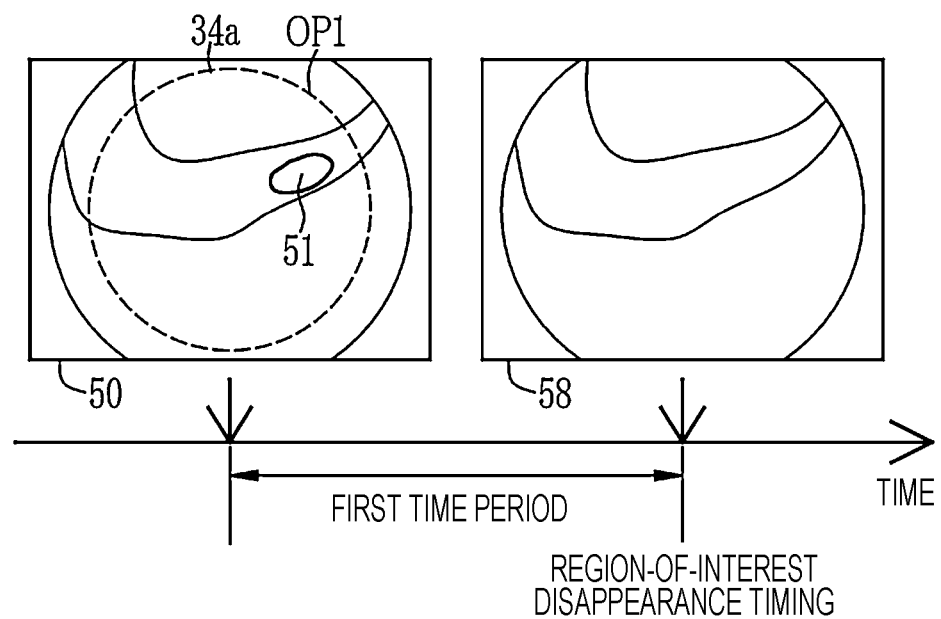
FIG. 9 is an explanatory diagram illustrating a first time period.

The details of the oversight determination processing performed by the oversight determination unit 46 will be described hereinafter. As illustrated in FIG. 9, the oversight determination unit 46 performs the oversight determination processing by using a first time period indicating a time period from when the region of interest 51 is detected at the first timing to when the region of interest 51 disappears from the first display region 34*a* of the monitor 34. A medical image 58 is an image obtained at a region-of-interest disappearance timing at which the region of interest 51 disappears from the first display region 34*a*. If the first time period is shorter than a second-determination first time period, the oversight determination unit 46 determines that the region of interest 51 is overlooked. The first time period is shorter than the second-determination first time period when, for example, the tip portion 40*a* of the endoscope 31 passes through the region of interest in the first part to be observed OP1 in a moment (for example, three frames).

Figure 10:
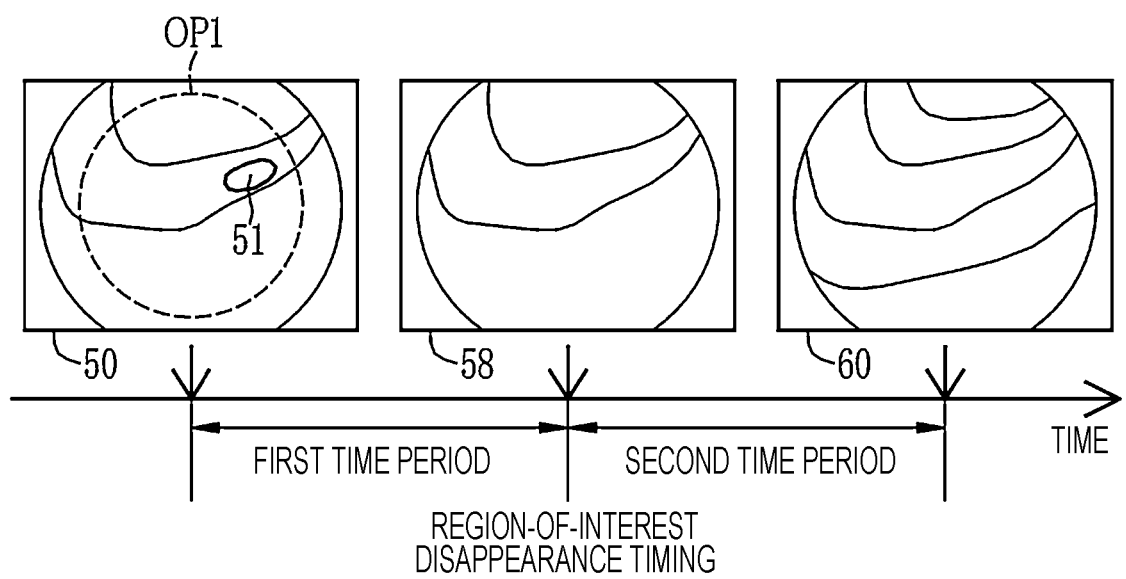
FIG. 10 is an explanatory diagram illustrating a second time period.

As illustrated in FIG. 10, the oversight determination unit 46 may perform the oversight determination processing by using, in addition to the first time period, a second time period indicating a time period that begins after the region of interest 51 disappears from the first display region 34*a*. In this case, the oversight determination unit 46 determines that the region of interest 51 is overlooked when the first time period is shorter than the second-determination first time period and the second time period is longer than or equal to a second-determination second time period. The second time period is longer than or equal to the second-determination second time period when, for example, although the region of interest 51 disappears from the first display region 34a, the tip portion 40a does not return again to the region of interest in the first part to be observed OP1, without noticing the region of interest 51, even after a certain period of time (for example, 10 seconds) has elapsed. A medical image 60 is an image obtained at the point in time when the second time period elapses from the region-of-interest disappearance timing.

The first time period may be measured by measuring the time period itself or by using the number of frames or the time period in which the region-of-interest detection unit 45 detects the region of interest 51. The second time period may be measured by measuring the time period itself or by using the number of frames or the time period in which the region-of-interest detection unit 45 does not detect the region of interest 51. When the region-of-interest detection unit 45 measures the number of frames or the time period, it is preferable to measure the number of frames or the time period by using a detection result of a frame that is a certain period of time before the latest frame in consideration of potential detection error or detection failure caused by the region-of-interest detection unit 45.

Figure 11:
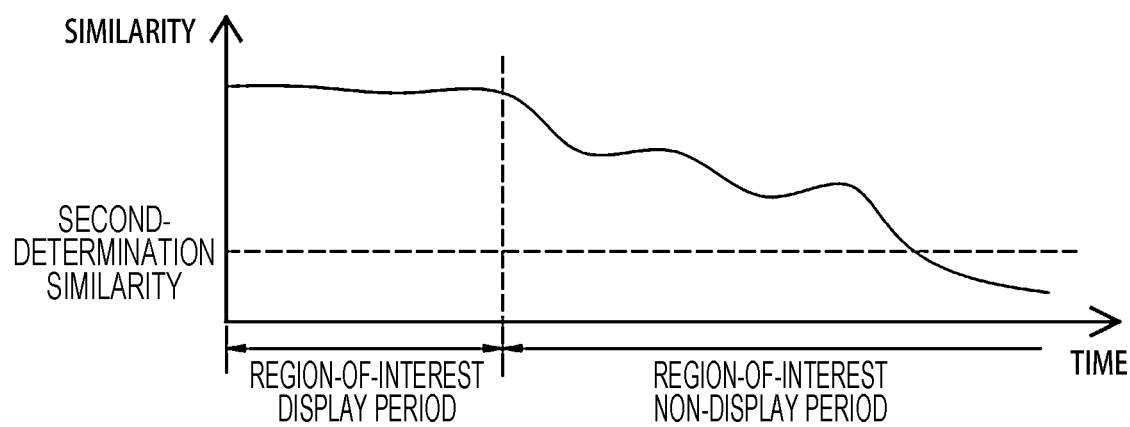
FIG. 11 is an explanatory diagram illustrating the similarity in a region-of-interest display period and a region-of-interest non-display period.

Further, the oversight determination unit 46 may perform the oversight determination processing by using the image similarity between a medical image acquired after the first timing and a medical image at the first timing. As illustrated in FIG. 11, since the region of interest 51 is included in a medical image at or after the first timing during a period (region-of-interest display period) in which the region of interest 51 is displayed in the first display region 34a, the image similarity to the medical image at the first timing is greater than or equal to a certain value. In a period (region-of-interest non-display period) during which the region of interest 51 has disappeared from the first display region 34a, in contrast, the region of interest 51 is not included in the medical image. Thus, the image similarity to the medical image at the first timing is very low. When the image similarity is lower than a second-determination similarity, the oversight determination unit 46 determines that the region of interest 51 in the first part to be observed OP is overlooked. The image similarity is preferably a value obtained as a result of comparison of the entire image or a value obtained by comparing feature values extracted from the image. The oversight determination unit 46 may perform oversight determination by combining at least one of the first time period or the second time period with the image similarity between a medical image acquired after the first timing and a medical image at the first timing.

Figure 12:
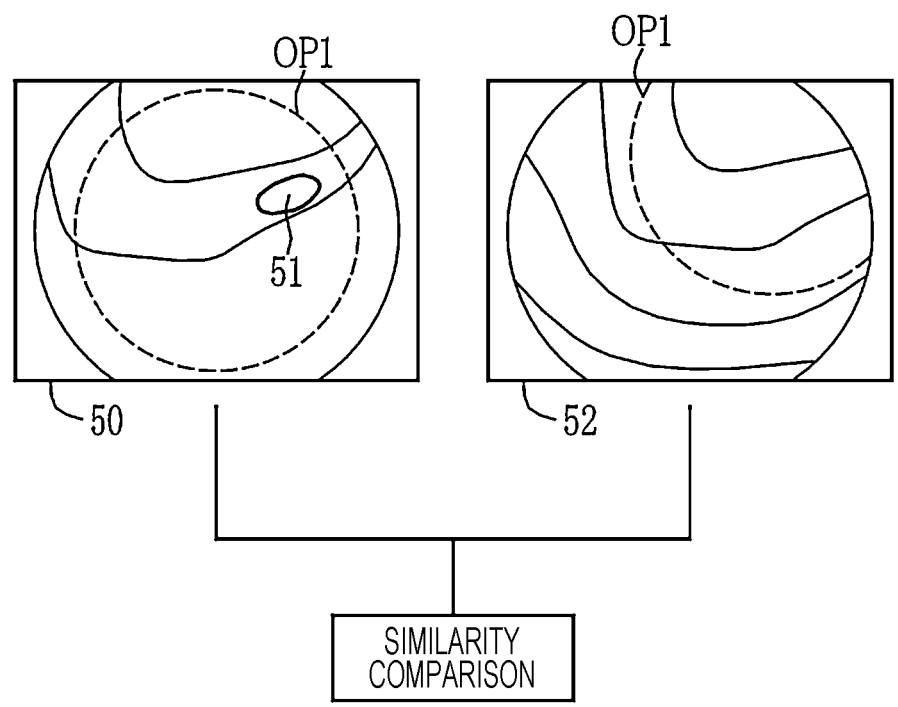
FIG. 12 is an explanatory diagram illustrating return determination processing using similarity.

The details of the return determination processing performed by the return determination unit 47 will be described hereinafter. The return determination unit 47 preferably performs the return determination processing by using the similarity between the medical image 52 at the second timing and the image of the first part to be observed OP1. The image similarity is preferably a value obtained as a result of comparison of the entire image between the medical image 52 at the second timing and the image of the first observation image or a value obtained by comparing feature values extracted from the images. As illustrated in FIG. 12, if the medical image 52 at the second timing includes a certain area or more of an image of the first part to be observed OP1, the return determination unit 47 determines that the tip portion 40a has returned to the first part to be observed OP1 when the similarity between the medical image 52 at the second timing and the image of the first part to be observed OP1 is greater than or equal to a first-determination similarity. In this way, by performing determination using the image similarity, it is possible to grasp that the tip portion 40a is located around the region of interest 51 even if the region of interest 51 is not detected.

Figure 13:
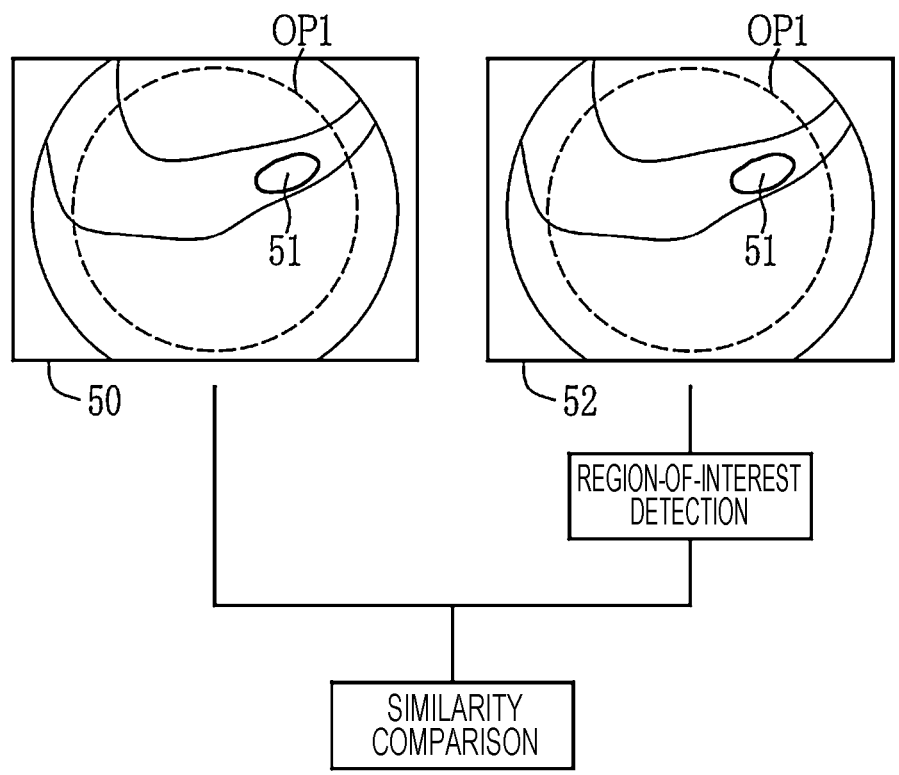
FIG. 13 is an explanatory diagram illustrating return determination processing using similarity and a detection result of the region of interest.

Further, the return determination unit 47 preferably performs the return determination processing by using the detection result of the region-of-interest detection unit 45 in addition to using the similarity between the medical image 52 at the second timing and the image of the first part to be observed OP1. As illustrated in FIG. 13, when the similarity between the medical image 52 at the second timing and the image of the first part to be observed OP1 is greater than or equal to the first-determination similarity and the region-of-interest detection unit 45 detects the region of interest 51, the return determination unit 47 determines that the tip portion 40a has returned to the first part to be observed OP1. When only the image similarity is used, a part to be observed similar to the first part to be observed OP may be erroneously determined as the first part to be observed OP1. In contrast, by using the detection result of the region of interest in addition to the image similarity, it is possible to perform the return determination processing with higher reliability.

Figure 14:
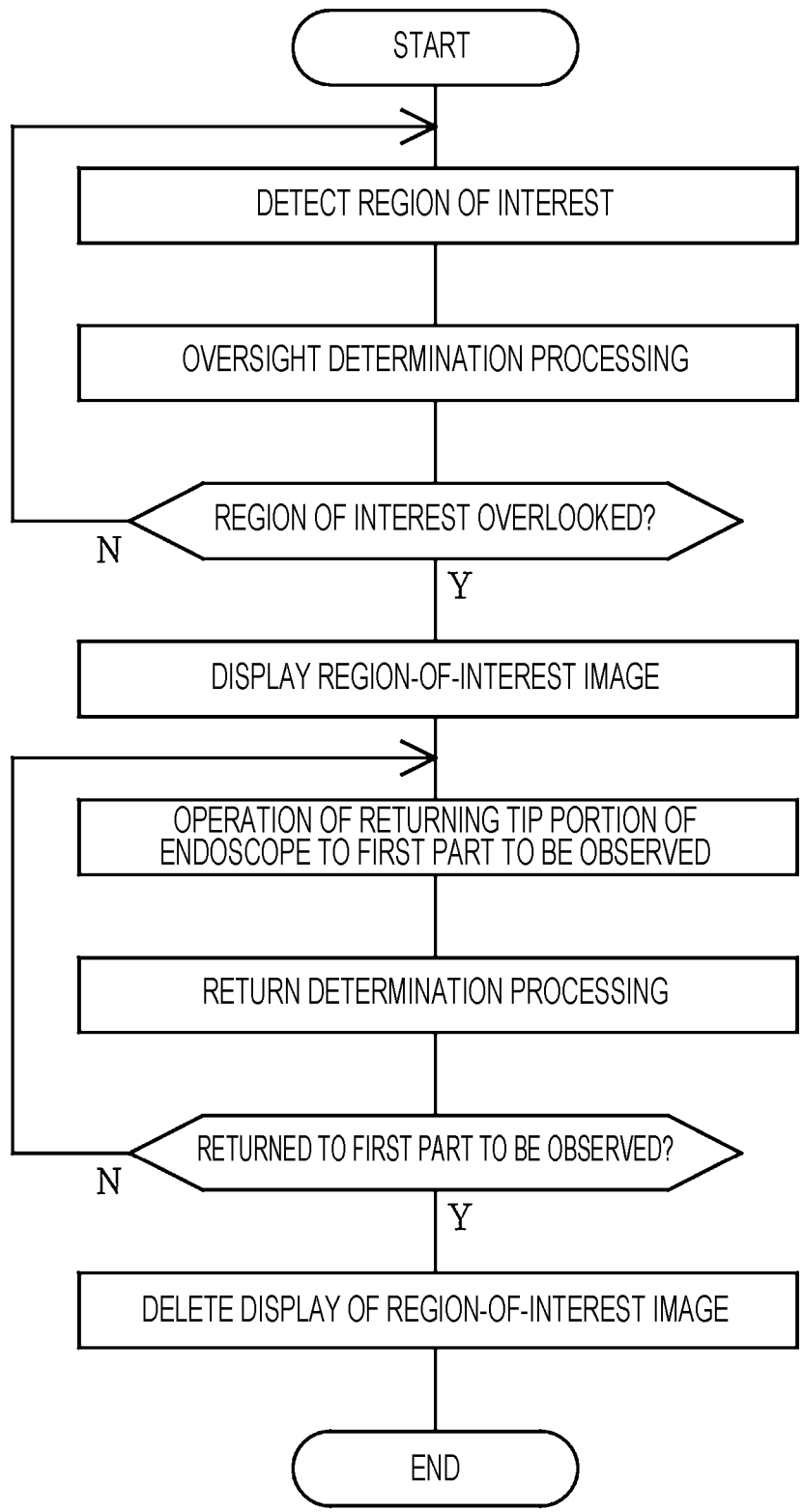
FIG. 14 is a flowchart illustrating the flow of a series of oversight determination processing and return determination processing.

Next, the flow of a series of oversight determination processing and return determination processing will be described with reference to a flowchart illustrated in FIG. 14. First, the region-of-interest detection unit 45 detects the region of interest 51 from the medical image 50 at the first timing. An image of the detected region of interest 51 is stored in the image storage unit (not illustrated) in the processor device 33 as a region-of-interest image. Then, the tip portion 40a of the endoscope 31 passes through the first part to be observed OP1 where the region of interest 51 is present without the user noticing the detection of the region of interest 51. As described above, in a case where the user overlooks the region of interest 51, the oversight determination unit 46 performs the oversight determination processing.

The oversight determination unit 46 performs the oversight determination processing by using the first time period from when the region of interest 51 is detected to when the region of interest 51 disappears from the first display region 34a of the monitor 34, the second time period indicating a time period that begins after the region of interest 51 disappears from the first display region 34a, or the similarity to the medical image 50 at the first timing. As a result of the oversight determination processing, if it is determined that the region of interest 51 is overlooked, the region-of-interest image stored in the image storage unit is displayed in the second display region 34b of the monitor 34. On the other hand, as a result of the oversight determination processing, if it is determined that the region of interest 51 is not overlooked, the region-of-interest image 55 is not displayed in the second display region 34b of the monitor 34.

If the user notices the region-of-interest image displayed in the second display region 34b, the user operates the endoscope 31 to perform an operation of returning the tip portion 40a of the endoscope 31 to the first part to be observed OP. To allow the user to grasp whether the tip portion 40a has returned to the first part to be observed OP1, the return determination unit 47 performs return determination processing. The return determination unit 47 performs the return determination processing by using the similarity between the medical image 52 obtained at the second timing different from the first timing and the medical image 50 at the first timing or the detection result of the region-of-interest detection unit 45. As a result of the return determination processing, if it is determined that the tip portion 40$a$ has returned to the first part to be observed OP1, the display of the region-of-interest image 55 in the second display region 34$b$ is deleted, or an enhanced image is displayed in the second display region 34$b$. The return determination processing is repeatedly performed until it is determined that the tip portion 40$a$ has returned to the first part to be observed OP1.

Figure 15:
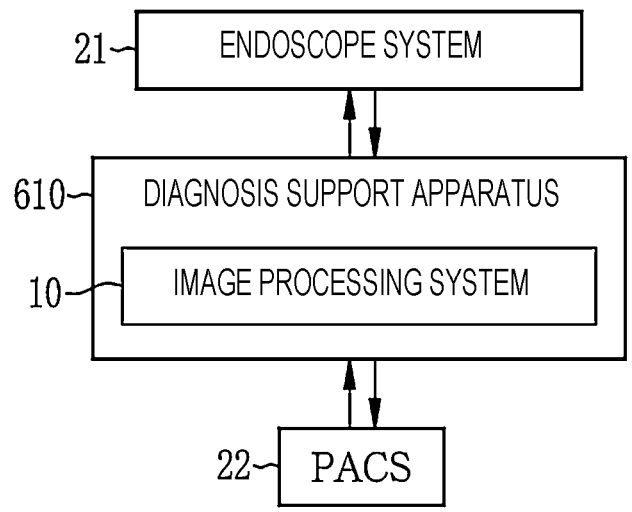
FIG. 15 is a schematic diagram illustrating a diagnosis support apparatus including the image processing system.
Figure 16:
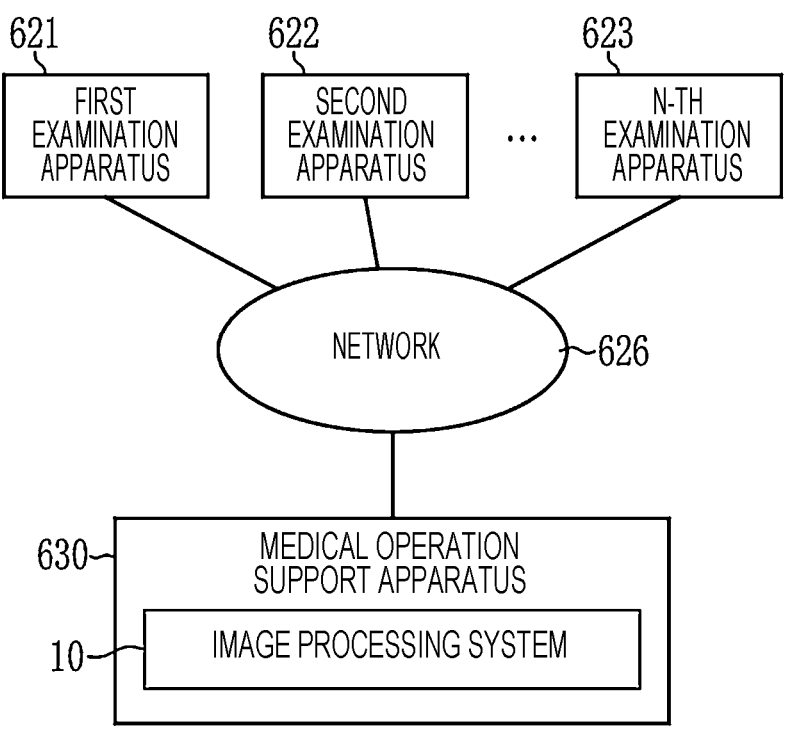
FIG. 16 is a schematic diagram illustrating a medical operation support apparatus including the image processing system.

As illustrated in FIG. 15, a diagnosis support apparatus 610 to be used in combination with the endoscope system 21 or any other modality and the PACS 22 can include the image processing system 10 according to the embodiment described above and other modifications. As illustrated in FIG. 16, for example, a medical operation support apparatus 630 including the endoscope system 21 and to be connected to various examination apparatuses such as a first examination apparatus 621, a second examination apparatus 622, . . . , and an N-th examination apparatus 623 via a desired network 626 can include the image processing system 10 according to the embodiment described above and other modifications.

Additionally, the image processing system 10, the endoscope system 21, and various apparatuses or systems including the image processing system 10 can be used with various modifications or the like described below.

As the medical image, a normal light image obtained by irradiation with light in the white range or, as light in the white range, light in a plurality of wavelength ranges.

When an image obtained by irradiation with light in a specific wavelength range is used as the medical image, the specific wavelength range may be a range narrower than the white wavelength range.

The specific wavelength range is, for example, the blue range or green range in the visible range.

When the specific wavelength range is the blue range or green range in the visible range, preferably, the specific wavelength range includes a wavelength range greater than or equal to 390 nm and less than or equal to 450 nm or greater than or equal to 530 nm and less than or equal to 550 nm, and light in the specific wavelength range has a peak wavelength in a wavelength range greater than or equal to 390 nm and less than or equal to 450 nm or greater than or equal to 530 nm and less than or equal to 550 nm.

The specific wavelength range is, for example, the red range in the visible range.

When the specific wavelength range is the red range in the visible range, preferably, the specific wavelength range includes a wavelength range greater than or equal to 585 nm and less than or equal to 615 nm or greater than or equal to 610 nm and less than or equal to 730 nm, and light in the specific wavelength range has a peak wavelength in a wavelength range greater than or equal to 585 nm and less than or equal to 615 nm or greater than or equal to 610 nm and less than or equal to 730 nm.

The specific wavelength range may include, for example, a wavelength range in which a light absorption coefficient is different between oxyhemoglobin and reduced hemoglobin, and light in the specific wavelength range may have a peak wavelength in a wavelength range in which a light absorption coefficient is different between oxyhemoglobin and reduced hemoglobin.

When the specific wavelength range includes a wavelength range in which a light absorption coefficient is different between oxyhemoglobin and reduced hemoglobin, and light in the specific wavelength range has a peak wavelength in a wavelength range in which a light absorption coefficient is different between oxyhemoglobin and reduced hemoglobin, preferably, the specific wavelength range includes a wavelength range of 400±10 nm, 440±10 nm, 470±10 nm, or greater than or equal to 600 nm and less than or equal to 750 nm, and light in the specific wavelength range has a peak wavelength in a wavelength range of 400±10 nm, 440±10 nm, 470±10 nm, or greater than or equal to 600 nm and less than or equal to 750 nm.

When the medical image is an in-vivo image obtained by imaging of the inside of a living body, the in-vivo image may have information on fluorescence emitted from a fluorescent substance in the living body.

As the fluorescence, fluorescence obtained by irradiation of the inside of a living body with excitation light having a peak wavelength greater than or equal to 390 nm and less than or equal to 470 nm may be used.

When the medical image is an in-vivo image obtained by imaging of the inside of a living body, the wavelength range of infrared light may be used as the specific wavelength range described above.

When the medical image is an in-vivo image obtained by imaging of the inside of a living body and the wavelength range of infrared light is used as the specific wavelength range described above, preferably, the specific wavelength range includes a wavelength range greater than or equal to 790 nm and less than or equal to 820 nm or greater than or equal to 905 nm and less than or equal to 970 nm, and light in the specific wavelength range has a peak wavelength in a wavelength range greater than or equal to 790 nm and less than or equal to 820 nm or greater than or equal to 905 nm and less than or equal to 970 nm.

The medical image acquisition unit 11 can have a special light image acquisition unit that acquires a special light image having a signal in the specific wavelength range on the basis of a normal light image obtained by irradiation with light in the white range or, as light in the white range, light in a plurality of wavelength ranges. In this case, the special light image can be used as the medical image.

The signal in the specific wavelength range can be obtained by calculation based on color information of RGB or CMY included in the normal light image.

A feature value image generation unit can be included that generates a feature value image by using calculation based on at least one of a normal light image obtained by irradiation with light in the white range or, as light in the white range, light in a plurality of wavelength ranges and a special light image obtained by irradiation with light in the specific wavelength range. In this case, the feature value image can be used as the medical image.

In the endoscope system 21, a capsule endoscope can be used as the endoscope 31. In this case, the light source device 32 and a portion of the processor device 33 can be mounted in the capsule endoscope.

In the embodiment described above and modifications, the hardware structure of processing units that execute various types of processing, such as the medical image acquisition unit 11, the medical image analysis processing unit 12, the display control unit 15, the input receiving unit 16, the overall control unit 17, the medical image acquisition unit 35, the medical image analysis processing unit 36, the display control unit 37, the region-of-interest detection unit 45, the oversight determination unit 46, and the return determination unit 47, is implemented as various processors described hereinbelow. The various processors include a CPU (Central Processing Unit), which is a general-purpose processor executing software (program) to function as various processing units, a programmable logic device (PLD) such as an FPGA (Field Programmable Gate Array), which is a processor whose circuit configuration is changeable after manufacture, a dedicated electric circuit, which is a processor having a circuit configuration specifically designed to execute various types of processing, a GPU (Graphical Processing Unit), which is an arithmetic unit or a processor specific to real-time image processing, and so on.

A single processing unit may be configured as one of the various processors or as a combination of two or more processors of the same type or different types (for example, a plurality of FPGAs, a combination of a CPU and an FPGA, or a combination of a CPU and a GPU). Alternatively, a plurality of processing units may be configured as a single processor. Examples of configuring a plurality of processing units as a single processor include, first, a form in which, as typified by a computer such as a client or a server, the single processor is configured as a combination of one or more CPUs and software and the processor functions as the plurality of processing units. The examples include, second, a form in which, as typified by a system on chip (SoC) or the like, a processor is used in which the functions of the entire system including the plurality of processing units are implemented as one IC (Integrated Circuit) chip. As described above, the various processing units are configured by using one or more of the various processors described above as a hardware structure.

More specifically, the hardware structure of these various processors is an electric circuit (circuitry) in which circuit elements such as semiconductor elements are combined.

Another embodiment of the present invention provides a medical image processing system including
a processor device,
the processor device being configured to
acquire, using a medical image acquisition unit, a medical image obtained by imaging of an observation target,
detect, using a region-of-interest detection unit, a region of interest located in a first part to be observed within the observation target from a medical image acquired at a first timing,
perform, using a first determination unit, first determination processing for determining, in a case where the tip portion moves away from the first part to be observed and moves toward a second part to be observed different from the first part to be observed, and then the tip portion moves away from the second part to be observed and moves toward the first part to be observed, whether the tip portion has returned to the first part to be observed, by using a medical image acquired at a second timing different from the first timing, and
perform, using a display control unit, display control of a display unit by using a determination result of the first determination unit.

REFERENCE SIGNS LIST 10 image processing system
11 medical image acquisition unit
12 medical image analysis processing unit
13 display unit
15 display control unit
16 input receiving unit
17 overall control unit
18 storage unit
21 endoscope system
22 PACS
31 endoscope
32 light source device
33 processor device
34 monitor
34a first display region
34b second display region
35 medical image acquisition unit
36 medical image analysis processing unit
37 display control unit
40 insertion section
40a tip portion
41 operation section
42 imaging element
45 region-of-interest detection unit
46 oversight determination unit
47 return determination unit
50 medical image
51 region of interest
52 medical image
55 region-of-interest image
56 enhanced image
58 medical image
60 medical image
610 diagnosis support apparatus
621 first examination apparatus
622 second examination apparatus
623 N-th examination apparatus
626 network
630 medical operation support apparatus
OP1 first part to be observed
OP2 second part to be observed

What is claimed is:

1. An endoscope system comprising:
an endoscope having disposed in a tip portion thereof an imaging element that performs imaging of an observation target and outputs a medical image;
a processor configured to function as:
a medical image acquisition unit that acquires the medical image;
a region-of-interest detection unit that detects a region of interest located in a first part to be observed within the observation target from a medical image acquired at a first timing;
a first determination unit that performs first determination processing for determining, in a case where the tip portion moves away from the first part to be observed and moves toward a second part to be observed different from the first part to be observed, and then the tip portion moves away from the second part to be observed and moves toward the first part to be observed, whether the tip portion has returned to the first part to be observed, by using a medical image acquired at a second timing different from the first timing;
a display control unit that performs display control of a display by using a determination result of the first determination unit; and
a second determination unit that performs second determination processing for determining whether the region of interest in the first part to be observed is overlooked,
wherein the display control unit performs the display control by using the determination result of the first determination unit and a determination result of the second determination unit, and wherein the second determination unit performs the second determination processing by using a second time period indicating a time period that begins after the region of interest disappears from the display, and determines that the region of interest in the first part to be observed is overlooked when the second time period is longer than or equal to a second-determination second time period.

2. The endoscope system according to claim 1, wherein the first determination unit performs the first determination processing by using a similarity between the medical image at the first timing and the medical image at the second timing.

3. The endoscope system according to claim 2, wherein the first determination unit determines that the tip portion has returned to the first part to be observed when the similarity is greater than or equal to a first-determination similarity.

4. The endoscope system according to claim 2, wherein the first determination unit determines that the tip portion has returned to the first part to be observed when the similarity is greater than or equal to a first-determination similarity and the region-of-interest detection unit detects the region of interest in the first part to be observed.

5. The endoscope system according to claim 1, wherein the second determination unit performs the second determination processing by further using a first time period indicating a time period from when the region of interest in the first part to be observed is detected to when the region of interest disappears from the display.

6. The endoscope system according to claim 5, wherein the second determination unit determines that the region of interest in the first part to be observed is overlooked when the first time period is shorter than a second-determination first time period and the second time period is longer than or equal to the second-determination second time period.

7. The endoscope system according to claim 1, wherein the second determination unit performs the second determination processing by further using a similarity between the medical image acquired by the medical image acquisition unit and the medical image at the first timing.

8. The endoscope system according to claim 1, wherein the display control unit performs display control for a region-of-interest image at an oversight determination timing at which it is determined in the second determination processing that the region of interest in the first part to be observed is overlooked and at a return determination timing at which it is determined that the tip portion has returned to the first part to be observed, the region-of-interest image being an image displaying the region of interest in the first part to be observed.

9. The endoscope system according to claim 8, wherein the display control unit starts displaying the region-of-interest image at the oversight determination timing and keeps displaying the region-of-interest image during a period from the oversight determination timing to the return determination timing.

10. The endoscope system according to claim 9, wherein the display control unit hides the region-of-interest image at the return determination timing.

11. The endoscope system according to claim 9, wherein the display control unit displays an enhanced image at the return determination timing, the enhanced image being obtained by performing enhancement processing on the region-of-interest image.

12. A medical image processing system comprising:
a processor configured to function as:
a medical image acquisition unit that acquires a medical image obtained by imaging of an observation target;
a region-of-interest detection unit that detects a region of interest located in a first part to be observed within the observation target from a medical image acquired at a first timing;
a first determination unit that performs first determination processing for determining whether a medical image acquired at a second timing different from the first timing includes at least a portion of an image of the first part to be observed; and
a display control unit that performs display control of a display by using a determination result of the first determination unit; and
a second determination unit that performs second determination processing for determining whether the region of interest in the first part to be observed is overlooked,
wherein the display control unit performs the display control by using the determination result of the first determination unit and a determination result of the second determination unit, and
wherein the second determination unit performs the second determination processing by using a second time period indicating a time period that begins after the region of interest disappears from the display, and determines that the region of interest in the first part to be observed is overlooked when the second time period is longer than or equal to a second-determination second time period.

13. The endoscope system according to claim 12, wherein the second determination unit performs the second determination processing by further using a first time period indicating a time period from when the region of interest in the first part to be observed is detected to when the region of interest disappears from the display.

14. The endoscope system according to claim 13, wherein the second determination unit determines that the region of interest in the first part to be observed is overlooked when the first time period is shorter than a second-determination first time period and the second time period is longer than or equal to the second-determination second time period.

* * * * *